(12) United States Patent
Murray et al.

(10) Patent No.: US 10,359,419 B2
(45) Date of Patent: *Jul. 23, 2019

(54) METHODS FOR DETECTION OF TARGET USING AFFINITY BINDING

(71) Applicant: General Electric Company, Schenectady, NY (US)

(72) Inventors: Anthony John Murray, Lebanon, NJ (US); Radislav Alexandrovich Potyrailo, Niskayuna, NY (US); Andrew David Pris, Altamont, NY (US); Nandini Nagraj, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 539 days.

This patent is subject to a terminal disclaimer.

(21) Appl. No.: 14/043,887

(22) Filed: Oct. 2, 2013

(65) Prior Publication Data

US 2015/0093820 A1  Apr. 2, 2015

(51) Int. Cl.
 *G01N 33/53* (2006.01)
 *G01N 33/532* (2006.01)
 *G01N 33/58* (2006.01)

(52) U.S. Cl.
 CPC ....... *G01N 33/5308* (2013.01); *G01N 33/532* (2013.01); *G01N 33/58* (2013.01)

(58) Field of Classification Search
 None
 See application file for complete search history.

(56) References Cited

U.S. PATENT DOCUMENTS

| | | | |
|---|---|---|---|
| 4,912,032 A * | 3/1990 | Hoffman | A61K 9/2027 435/7.1 |
| 5,683,916 A | 11/1997 | Goffe et al. | |
| 5,714,320 A | 2/1998 | Kool | |
| 5,998,588 A * | 12/1999 | Hoffman | B82Y 5/00 424/178.1 |
| 6,258,275 B1 | 7/2001 | Freitag et al. | |
| 6,287,772 B1 | 9/2001 | Stefano et al. | |
| 6,426,086 B1 | 7/2002 | Papahadjopoulos et al. | |
| 6,867,268 B2 | 3/2005 | Vaidya et al. | |
| 7,157,603 B2 | 1/2007 | Hilbrig | |
| 7,371,852 B2 | 5/2008 | Hardeman et al. | |
| 2002/0076704 A1 | 6/2002 | Weissman et al. | |
| 2002/0155478 A1 | 10/2002 | Nelson et al. | |
| 2003/0044794 A1 | 3/2003 | Bandaru et al. | |
| 2005/0037075 A1 * | 2/2005 | Farokhzad | A61K 47/48192 424/468 |
| 2005/0176940 A1 | 8/2005 | King | |
| 2005/0208487 A1 * | 9/2005 | Burmeister | B01J 20/289 435/6.11 |
| 2006/0127925 A1 * | 6/2006 | Stayton | C12N 15/1006 435/6.12 |
| 2006/0172318 A1 * | 8/2006 | Medinz | B82Y 5/00 435/6.11 |
| 2008/0096975 A1 * | 4/2008 | Guan | A61K 9/0019 514/772.3 |
| 2008/0182759 A1 | 7/2008 | West et al. | |
| 2008/0206894 A1 * | 8/2008 | Lyon | G01N 33/54353 436/531 |
| 2008/0255027 A1 * | 10/2008 | Moya | C07K 1/32 514/1.1 |
| 2008/0293926 A1 | 11/2008 | Hallgren et al. | |
| 2009/0075834 A1 | 3/2009 | Doyle et al. | |
| 2010/0018876 A1 | 1/2010 | Crothers et al. | |
| 2010/0028953 A1 | 2/2010 | Koch et al. | |
| 2010/0055068 A1 | 3/2010 | Santerre et al. | |
| 2010/0151465 A1 | 6/2010 | Ju et al. | |
| 2010/0152056 A1 | 6/2010 | Lopreato | |
| 2011/0136099 A1 * | 6/2011 | Schneider | G01N 33/5308 435/5 |
| 2011/0190483 A1 | 8/2011 | Jayawickramarajah | |
| 2011/0251088 A1 | 10/2011 | Lopreato | |
| 2012/0010390 A1 | 1/2012 | Van Alstine et al. | |
| 2012/0115752 A1 | 5/2012 | Zichi et al. | |
| 2012/0322681 A1 | 12/2012 | Kung et al. | |

FOREIGN PATENT DOCUMENTS

| | | | |
|---|---|---|---|
| EP | 2589657 A1 | 5/2013 | |
| WO | 2007117444 A2 | 10/2007 | |
| WO | 2011060557 A1 | 5/2011 | |

OTHER PUBLICATIONS

Mattiasson et al., Metal-chelate affinity precipitation of proteins using responsive polymers, Nature Protocols, (2)(1), 2007, 213-220.*
Ho et al., Environmental considerations in biologics manufacturing, Green Chem., 2010, 12, 755-766.*
Isik et al., Thermoresponsive Poly(N-isopropylacrylamide-coN-vinylimidazole) Hydrogels by Redox Polymerization, Advances in Polymer Technology, vol. 22, No. 3, 246-251 (2003).*
Okhapkin et al., Thermosensitive Imidazole-Containing Polymers as Catalysts in Hydrolytic Decomposition of p-Nitrophenyl Acetate, Macromolecules 2004, 37, 7879-788.*
Majd et al., "The Affinity Precipitation for the Isolation of Biomolecules", Thesis, Ecole Polytechnique Federale de Lausanne, pp. 1-146, 2007.

(Continued)

*Primary Examiner* — Andrea S Grossman
(74) *Attorney, Agent, or Firm* — Eversheds Sutherland (US) LLP

(57) ABSTRACT

A method of recovering a target from a sample is provided. The method comprises the adding a substrate coupled binding element to the sample comprising the target to form a substrate coupled binding element-target complex; precipitating the complex by changing one or more environmental conditions of the substrate and recovering the target and the substrate coupled binding-element under mild conditions.

26 Claims, 2 Drawing Sheets

(56) References Cited

OTHER PUBLICATIONS

Ashok Kumar et al., "Smart Polymers: Physical Forms and Bioengineering Applications", Available online at www.sciencedirect.com, Received Feb. 22, 2007, received in revised form May 22, 2007, accepted May 22, 2007, Prog. Polym. Sci. 32 (2007) 1205-1237.

Ashwani K. Sharma et al., "Small-Molecule-Dependent Split Aptamer Ligation", Department of Chemistry and the Center for Cell and Genome Science, University of Utah, Salt Lake City, Utah 84112, United States, Journal of the American Chemical Society, 4 Pages.

Eric Stern et al., "Label-free biomarker detection from whole blood", Advance online Publication, www.nature.com, naturenanotechnology, 5 Pages.

Lindsay Arnold et al., "Novel thermo-responsive fucose binding ligands for glycoprotein purification by affinity precipitation", Received Jun. 25, 2013, 19 Pages.

Burmistrova et al., "The Effect of Co-Monomer Content on the Swelling/Shrinking and Mechanical Behaviour of Individually Adsorbed PNIPAM Microgel Particles", Polymers, vol. No. 3, pp. 1575-1590, 2011.

Wang et al., "Ultrasensitive Detection of Protein Using an Aptamer-Based Exonuclease Protection Assay", Analytical Chemistry, vol. No. 76, Issue No. 19, pp. 5605-5610, Oct. 1, 2004.

Mairal et al., "Aptamers: Molecular Tools for Analytical Applications", Analytical and Bioanalytical Chemistry, vol. No. 390, Issue No. 4, pp. 989-1007, Jun. 21, 2007.

PCT Search Report and Written Opinion issued in connection with corresponding PCT Application No. PCT/US2014/055055 dated Dec. 10, 2014.

Ellington et al., "In vitro selection of RNA molecules that bind specific ligands", Nature Aug. 1990, vol. 346, pp. 818-822.

Tuerk et al., "Systematic evolution of ligands by exponential enrichment: RNA ligands to bacteriophage T4 DNA polymerase", Science, Aug. 1990, vol. 249, pp. 505-510.

Hermann et al., Adaptive recognition by nucleic acid aptamers, Science Feb. 2000, vol. 287, pp. 820-825.

Famulok et al., "Aptamer modules as sensors and detectors", Accounts of Chemical Research, 2011, vol. 44, No. 12, pp. 1349-1358.

Potyrailo et al., "Polymeric Sensor Materials: Toward an Alliance of Combinatorial and Rational Design Tools?", Angew. Chem. Int. Ed. 2006, vol. 45, pp. 702-723.

Sefah et al., "Development of DNA aptamers using Cell—SELEX", Nature Protocols 2010, vol. 5, No. 6, pp. 1169-1185.

Kimoto et al., "Generation of high—affinity DNA aptamers using an expanded genetic alphabet", Nature Biotechnology 2013, vol. 31, No. 5, pp. 453-457.

Švitel et al., "Surface plasmon resonance based pesticide assay on a renewable biosensing surface using the reversible concanavalin a monosaccharide interaction", Biosensors Bioelectronics, 2000, vol. 15, pp. 411-415.

Choi et al., "Reusable biosensors via in situ electrochemical surface regeneration in microfluidic applications", Biosensors Bioelectronics, 2009, vol. 25, pp. 527-531.

Xu et al., "Label—free impedimetric thrombin sensor based on poly(pyrrole—nitrilotriacetic acid)—aptamer film", Biosensors Bioelectronics, 2013, vol. 41, pp. 90-95.

Radi et al., "Reagentless, Reusable, Ultrasensitive Electrochemical Molecular Beacon Aptasensor", J. Am. Chem. Soc. 2006, vol. 128, pp. 117-124.

Potyrailo, R. A. et al., "Adapting selected nucleic acid ligands (aptamers) to biosensors", Analytical Chemistry, 1998, vol. 70, No. 16, pp. 3419-3425.

Yao, C. et al., "Aptamer—based piezoelectric quartz crystalmicrobalance biosensor array for the quantification of IgE", Biosensors and Bioelectronics 2009, vol. 24, pp. 2499-2503.

Guo, L. et al., "Reusable plasmonic aptasensors:Using a single nanoparticle to establish a calibration curve and to detect analytes", ChemComm 2011, vol. 47, pp. 7125-7127.

Wijesuriya, D. et al., "Regeneration of immobilized antibodies on fiber optic probes", Biosensors & Bioelectronics 1994, vol. 9, pp. 585-592.

Andersson, K. et al., "Identification and optimization of regeneration conditions for affinity—based biosensor assay. A multivariate cocktail approach", Analytical Chemistry, 1999, vol. 71, No. 13, pp. 2475-2481.

Kandimalla, V. B. et al. "Regeneration of ethyl parathion antibodies for repeated use in immunosensor: a study on dissociation of antigens from antibodies", Biosensors and Bioelectronics 2004, vol. 20, pp. 903-906.

Drake, A. W. et al., "A strategic and systematic approach for the determination of biosensor regeneration conditions", Journal of Immunological Methods 2011, vol. 371, pp. 165-169.

Liss, M. et al., "An aptamer—based quartz crystal protein biosensor", Analytical Chemistry, 2002, vol. 74, No. 17, pp. 4488-4495.

Yao, C. et al., "Development of a Quartz Crystal Microbalance Biosensor with Aptamers as Bio—recognition Element", Sensors 2010, vol. 10, pp. 5859-5871.

Bock, L. C. et al., "Selection of single—stranded DNA molecules that bind and inhibit human thrombin", Nature 1992, vol. 355, pp. 564-566.

Chilkoti, A. et al., "Molecular Origins of the Slow Streptavidin—Biotin Dissociation Kinetics", J. American Chemical Society 1995, vol. 117, pp. 10622-10628.

Piran, U. et al., "Dissociation rate constant of the biotin—streptavidin complex", Journal of Immunological Methods 1990, vol. 133, pp. 141-143.

Lin, S. et al, "Characterization of the 'helix clamp' motif of HIV—1 reverse transcriptase using MALDI—TOF MS and surface plasmon resonance", AAnalytical Chemistry, 2000, vol. 72, pp. 2635-2640.

Freitag, R. et al., "Affinity precipitation an option for early capture in bioprocessing." Biotechnology Journal 2007, vol. 2, No. 6, pp. 685-690.

Galaev, I. Y. et al., "Affinity thermoprecipitation: Contribution of the efficiency of ligand—protein interaction and access of the ligand." Biotechnology and Bioengineering 1993, vol. 41, No. 11, pp. 1101-1106.

Miyakawa, S. et al., "Structural and molecular basis for hyperspecificity of RNA aptamer to human immunoglobulin G", 2008 RNA, vol. 14, No. 6, pp. 1154-1163.

Soh, N. et al., "Affinity Precipitation Separation of DNA Binding Protein Using Block Conjugate Composed of Poly (N-isopropylacrylamide) Grafted Double-Stranded DNA and Double-Stranded DNA Containing a Target Sequence". Analytical Sciences 2002, vol. 18, No. 12, pp. 1295-1299.

Walter, J.-G. et al., "Aptamers as affinity ligands for downstream processing", Engineering in Life Sciences 2012, vol. 12, No. 5, pp. 1-11.

Clark, et al., "Apamers as analytical regents". Electrophoresis 2002, vol. 23, pp. 1335-1340.

Dua, et al. "Patents on SELEX and Thorapcufic Aptanters". Recent Patents on DNA & Gene Sequences. 2008 pp. 172-186. vol. 2, No. 3. 2008.

Rajendran, et al., "Selecting Nucleic Acids for Biosonsor Applications". Combinatorial Chemistry & High Throughput Screening. 2002, vol. 5, pp. 263-270.

Cheng et al., "In vivo SELEX for Identification of Brain-penetrating Aptamers". Molecular Therapy Nucleic Acids. 2013, vol. 2, pp. 9.

Osborne et al., "Aptamers as therapeutic and diagnostic reagents: problems and prospects". Current Opinion in Chemical Biology 1997, vol. 1, pp. 5-9.

James "Aptamers" Encyclopedia of Analytical Chemistry. 2000, 23 pages.

Jhaveri et al., "In vitro selection of signaling aptamers". Nature Biotechnology. vol. 18, Dec. 2000, pp. 1293-1297.

Sampson "Protecting intellectual property rights in SELEX and aptamers" World Patent Information, 2003. 7 Pages.

(56) References Cited

OTHER PUBLICATIONS

Berezovski et al., "Non-SELEX: selection of aptamers without intermediate amplification of candidate oligonucleotides" Nature Protocols 2006, vol. 1, No. 3, 11 pages.
Subash Chandra Bose Gopinath "Methods developed for SELEX", Anal. Bioanal. Chem, 2007, vol. 387, pp. 171-182.

\* cited by examiner

US 10,359,419 B2

METHODS FOR DETECTION OF TARGET USING AFFINITY BINDING

FIELD OF INVENTION

The invention generally relates to methods for affinity precipitation using binding-elements.

BACKGROUND

Biopharmaceutical synthesis needs downstream processing for purification of biopharmaceutical products to remove contaminants that are undesirable. In biopharmaceutical synthesis, contaminants may include: host cell proteins, host cell nucleic acids, endotoxins (in the case of bacterial production systems), viruses (in the case of mammalian production systems), misfolded proteins, protein-aggregates and components that leach from chromatographic media. Various chromatographic techniques are typically used for removing the contaminants and affinity chromatography has been a successful attempt for its high specificity, selectivity and resolution.

Affinity chromatography is an effective initial step, following protein production and purification, however, cost and stability of affinity chromatography media, recovery of active product and predictability of optimal process conditions need radical improvement. Binding element, such as, affinity ligands, such as antibodies are valued for their high selectivity and affinity, however, the stability of the molecules due to their size and complex structure is an issue. Engineered protein binders have proved to be successful as affinity ligands for their small size, stability, and ease of synthesis in microbial production systems, however these binders might be unsuitable for therapeutic applications because of their potential immunogenicity. The protein based binders are generally expensive, and are not suitable for repeated use.

Binding-elements that offer reduced cost, better stability, high selectivity and specificity to target and fit to both the single-use and multiple use paradigms are highly desirable. Nucleic acid, namely DNA and RNA based binding-elements, such as aptamers have been developed that show enhanced stability and fit both the single-use and multi-use paradigms. An alternative method for using the binding-elements to identify and recover target efficiently under mild conditions, which ensures maintaining structural and functional integrity of the target molecule, is a long felt need.

BRIEF DESCRIPTION

In one embodiment, a method of recovering a target from a sample comprises adding a substrate coupled binding element to the sample comprising the target to form a substrate coupled binding element-target complex; precipitating the substrate coupled binding element-target complex by changing one or more environmental conditions of the substrate; and recovering the target and the substrate coupled binding-element separately from the precipitated complex under mild condition.

In another embodiment, a method of recovering a target from a sample comprises providing a thermoresponsive polymer coupled binding element in contact with the sample comprising the target to form a thermoresponsive polymer coupled binding element-target complex; precipitating the thermoresponsive polymer coupled binding element-target complex; washing the precipitate to remove unbound or non-specifically bound molecules; re-suspending the precipitate to a solution and dissociating the complex under mild condition to release the thermoresponsive polymer coupled binding element and the target; re-precipitating the thermoresponsive polymer coupled binding element forming a supernatant comprising the target; and recovering the target from the supernatant.

In another embodiment of a method of recovering plurality of targets from a sample, the method comprises adding plurality of substrate coupled binding elements to the sample comprising plurality of targets to form plurality of substrate coupled binding element-target complexes; precipitating the substrate coupled binding element-target complexes by changing one or more environmental conditions of the substrate; recovering the targets and the substrate coupled binding-elements separately from the precipitated complex under mild conditions.

In one embodiment, a method of recovering a target from a sample in a sterile biopharmaceutical manufacturing process, comprises adding a substrate coupled binding element to the sample comprising the target to form a substrate coupled binding element-target complex; precipitating the substrate coupled binding element-target complex by changing one or more environmental conditions of the substrate; and recovering the target and the substrate coupled binding-element separately from the precipitated complex under mild condition for one or more times maintaining sterility of the manufacturing process.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
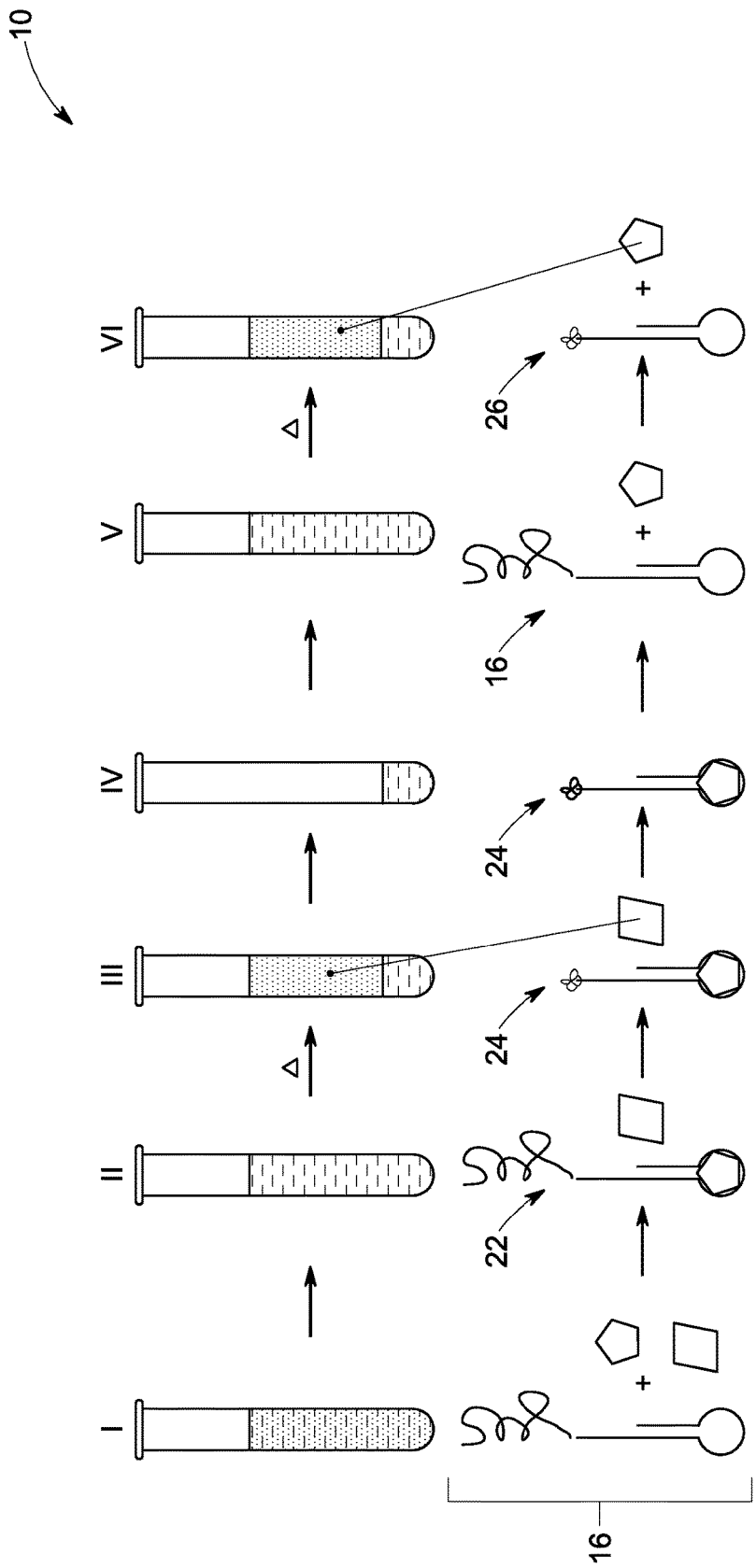
FIG. 1 is a schematic representation showing method of affinity precipitation using substrate coupled binding-elements for detecting specific target molecules in accordance with one embodiment of the invention.

The methods for target binding and recovery using binding-elements are provided. The binding-elements have higher specificity and selectivity for the target molecules. The methods for detecting a target and purification using binding elements are reliable and suitable for applications such as affinity purification of target molecules from a population of molecules having structure similar to the target.

To more clearly and concisely describe and point out the subject matter of the claimed invention, the following definitions are provided for specific terms, which are used in the following description and the appended claims. Throughout the specification, exemplification of specific terms should be considered as non-limiting examples.

The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Similarly, "free" may be used in combination with a term, and may include an insubstantial number, or trace amounts while still being considered free of the modified term. Where necessary, ranges have been supplied, and those ranges are inclusive of all sub-ranges there between.

As used herein the term "nucleotide" or "nucleotide base" refers to a nucleoside phosphate. The term includes, but is not limited to, a natural nucleotide, a synthetic nucleotide, a modified nucleotide, or a surrogate replacement moiety (e.g., inosine). The nucleoside phosphate may be a nucleoside monophosphate, a nucleoside diphosphate or a nucleoside triphosphate. The sugar moiety in the nucleoside phosphate may be a pentose sugar, such as ribose, and the phosphate esterification site may correspond to the hydroxyl group attached to the C-5 position of the pentose sugar of the nucleoside. A nucleotide may be, but is not limited to, a deoxyribonucleotide triphosphate (dNTP) or a nucleotide triphosphate (NTP). The nucleotides may be represented using alphabetical letters, for example, A denotes adenosine (e.g., a nucleotide containing the nucleobase, adenine), C denotes cytosine, G denotes guanosine, and T denotes thymidine.

As used herein, the term "oligonucleotide" refers to oligomers of nucleotides or derivatives thereof. The term "nucleic acid" as used herein refers to polymers of nucleotides or derivatives thereof. The term "sequence" as used herein refers to a nucleotide sequence of an oligonucleotide or a nucleic acid. Throughout the specification, whenever an oligonucleotide/nucleic acid is represented by a sequence of letters, the nucleotides are in 5'→3' order from left to right. The oligonucleotides/nucleic acids may be a DNA, an RNA, or their analogues (e.g., uracil, inosine analogue). The oligonucleotides or nucleic acids may also include modified bases and/or backbones (e.g., modified phosphate linkage such as thiophosphate or modified sugar moiety, such as locked nucleic acid). Non-limiting examples of synthetic backbones that confer stability and/or other advantages to the nucleic acids may include phosphorothioate linkages, peptide nucleic acid, locked nucleic acid, xylose nucleic acid, or analogues thereof. The oligonucleotide refers to a short linear oligonucleotide that may include 5 to 30 nucleotides. The oligonucleotides may also be interchangeably referred to herein as "oligomers" or "short oligomers". The oligonucleotide may be an RNA sequence, a DNA sequence, or a chimeric sequence comprising different bases. The oligonucleotide may contain natural, synthetic, or modified nucleotides. Both the upper and lower limits of the length of the oligonucleotide are empirically determined. The lower limit on oligonucleotide length is the minimum length that is required to form a transient complex upon binding with the target molecule under desired reaction conditions. Very short oligonucleotides (usually less than 3-4 nucleotides long) do not form thermodynamically stable complex with target molecule under such conditions. Generally, suitable oligonucleotide lengths are in the range of about 4 to about 30 nucleotides long.

In some embodiments, the oligonucleotide refers to a linear oligonucleotide that may include 5 to 1000 nucleotides. The upper limit of oligonucleotide length may be the maximum length that the linear oligonucleotide sequence be accurately amplified (usually around 1000-5000 nucleotides). Suitable oligonucleotide lengths may be in the range of 4-5000 nucleotides, or between 4-100 nucleotides long.

As used herein, the term "target molecule" refers to a molecule that is desired to be bound to one or more short oligomers present in the reaction mixture. For example, the target molecule may comprise a protein, a post-translationally modified protein, a peptide, a carbohydrate or a synthetic peptide. The target molecule is the molecule of interest, which either needs to be separated and purified out from a mixture of molecules or needs to be quantified or characterized.

The term "binding element" refers to herein as an oligonucleotide-based component that efficiently binds to a target molecule through one or more binding sites through different types of interactions, including but are not limited to, hydrophobic, Van der Waals interactions and hydrogen bonding. The binding element may include an aptamer, such as deoxyribonucleic acid (DNA) aptamer, ribonucleic acid (RNA) aptamer or peptide nucleic acid (PNA) aptamer.

One or more embodiments of the invention are directed to methods for detection and recovery of a target from a sample using binding-elements by affinity binding assays. In some embodiments, the method of recovering a target from a sample, comprises adding a substrate coupled binding element to the sample comprising the target to form a substrate coupled binding element-target complex. The substrate coupled binding element-target complex is further precipitated by changing one or more environmental conditions of the substrate and the target and the substrate coupled binding-element are recovered separately from the precipitated complex.

The target molecule and the binding-element are in contact, which enable the binding elements to bind to the target molecules and form a substrate coupled binding element-target complex. In some embodiments, the target molecule and the binding-element are mixed thoroughly to form a binding element-target complex in a first solution. In one or more embodiments, the target molecules and the binding elements are mixed in the first solution using different mixing techniques, such as by pipetting up and down, vortexing, mild shaking, waving or stirring. In one or more embodiments the target molecules and the binding element are incubated at a specific temperature without any mixing or agitation.

As noted, the method comprises addition of the sample to the binding element, wherein the target and the binding element may be in contact to each other, which results in formation of a substrate coupled binding element-target complex. In some embodiments, the plurality of binding-elements has affinity for the target molecules. As noted, the method comprises forming a binding-element-target complex. The term "binding-element-target complex" refers to a complex wherein a binding-element is bound to a target molecule. In some embodiments, the addition of substrate coupled binding element to the target forms a substrate coupled binding element-target complex. The term "binding element-target complex" or "complex" is interchangeably used hereinafter. In these embodiments, the first solution comprises the substrate coupled binding-element-target complex, excess unbound target, other molecules and impurities. As mentioned, the "other molecules", these molecules may have structural similarity with the target.

The affinity of the binding-element for the target molecules may enhance the binding efficiency of the binding-element to the target. In some embodiments, the binding-elements are bound to the target molecules by ionic interaction, H-bonding, Vander Waal's forces or combinations thereof. In some embodiments, the binding-element-target complex is stabilized by adding a reaction buffer to the mixture. The stability of the complex is desired as the complex is separated by precipitation. In one embodiment, the binding element-target complex comprises the binding element and the target in 1:1 ratio.

As noted, the substrate coupled binding element-target complex may be precipitated by changing one or more environmental conditions, forming a first supernatant. The non-limiting examples of environmental conditions may include temperature, pressure, pH, ionic strength, humidity and light. The precipitation of the binding element-target complex leaves non-specific, non-target molecules in the supernatant, which may be easily removable. The term "environmental condition" is used herein to indicate the physical or chemical changes induced to the substrate that leads to a conformational change to the substrate. For example, when the substrate comprises thermoresponsive polymer, the conformational changes occur to the substrate by increasing the temperature of the substrate above a lower critical solution temperature (LCST) of the substrate. The temperature change results in the conversion of liquid substrate (in solution state) to the insoluble substrate and the insoluble substrate is precipitated out from a solution.

As mentioned, adding a substrate coupled binding element to the sample forms a substrate coupled binding element-target complex followed by precipitation on changing environmental conditions, wherein the binding-element-target complex is desired to be stable enough to withstand environmental changes. The stability of the complex allows the recovery of complex as a precipitate. In some embodiments, the environmental conditions are defined as the conditions, which do not affect the stability of the complex.

The precipitate may be re-suspended to form a second solution using water or a buffer. In some embodiments, the substrate that is coupled to the binding-element is made of thermoresponsive polymer, wherein the precipitate of binding element-target complex is dissolved by changing the temperature of the second solution below the LCST of the thermoresponsive polymer. In solution state, such as in second solution, the binding element-target complex dissociates to form the target and the binding-element.

As noted, in some embodiments, the target dissociates from the substrate coupled binding element, wherein the dissociation of the binding element-target complex may be achieved by re-suspending the precipitated binding element-target complex forming a second solution. In some embodiments, in solution state, further dilution of the complex results in dissociation of the complex to the target and the substrate coupled binding element. In these embodiments, the target is eluted by inducing a conformational change to the target, binding element or binding element-target complex. For example, the manipulations that disrupt the secondary structure of the binding-element may lead to dissociation of the target molecule from the binding-element, enabling recovery of the target molecule using mild elution conditions. In some examples, a dissociation of the binding-element and the target molecule may be achieved by removal of divalent cations that stabilize the target-binding-element complex by use of a chelator. In an exemplary embodiment, the thrombin is used as a target and the binding-element specific to thrombin is dissociated by adding deionized water to the thrombin-binding-element complex.

The binding element-target complex may be dissociated to form the substrate coupled binding-element and the target, under mild conditions. The term "mild condition" refers to herein as a condition which causes a minimal structural change of the binding element so that it can release the target, however the condition ensures minimum or no structural or functional change to the target. The structural change may be reversible, so the original structure can be easily recovered. In some embodiments, the mild conditions allow recovery of the target in an un-denatured form with minimal aggregation or unfolding. In some embodiments, the mild condition causes a conformational change in the binding element and retains the intact structure and function of the target.

In some embodiments, when the mild condition causes minimum structural change to the target, the change is a reversible conformational change. In these embodiments, the target regains its original structure after recovery. For example, in the case of a nucleic acid based binding element, the conditions are selected that favor conformational change to the nucleic acid binding element however, maintains the tertiary structure and function of the target. As noted, the mild conditions allow for reuse of the binding element, such as re-use of thermo-precipitable binding element. In case of binding element used for detection or sensor applications, easy removal of analyte allows reuse of the sensor, preferably many times over with minimal loss of binding capacity or destruction of the binding element.

One or more examples of the mild condition may include, use of deionized water, weak bases, salts or chelators. The deionized water may un-shield the charge on the phosphate backbone of nucleic acids (such as DNA) and reduces the secondary structure. In some examples, dilute base, such as 0.1-50 mM may also be used to reduce secondary structure of the nucleic acids. The use of NaCl with a concentration of 1M or greater may also be used for effectively reducing ionic interactions. In some examples, the structure of the binding element is stabilized by metal ions, wherein the binding element may be destabilized using a metal chelator. In one embodiment, a liquid with low ionic strength, such as deionized water, is used to dissociate the target molecule. A liquid with low ionic strength is desired as the liquid helps in efficient downstream purification; for example buffer exchange.

In some embodiments, the method further comprises re-precipitating the substrate coupled binding element, which results in forming a second supernatant wherein the target is retained in the second supernatant. The substrate coupled binding element is re-precipitated by changing one or more environmental conditions, such as temperature, pressure, pH, ionic strength, humidity, exposure to light or combinations thereof. In one example, the substrate is made of thermoresponsive polymer, wherein the substrate is heated to attain a temperature above the LCST of the thermoresponsive polymers which results in re-precipitation, as heating above LCST renders the polymer more hydrophobic and thus less soluble in aqueous solution. In one or more embodiments, the substrate comprises two or more thermoresponsive polymers with different LCST.

As noted, the re-precipitation results in retaining the target in the second supernatant. The supernatant may be recovered by decanting, pipetting out, withdrawing by a pump, using centrifugation, using filtration or combinations thereof. The second supernatant comprising the target may be collected for downstream process and analysis. In some embodiments, the second supernatant is subjected to chromatographic separation to isolate different fractions of target for further purification of the target. For example, the supernatant is passed through an anion exchange HPLC column and fractions containing highest purity of the target are collected.

In some embodiments, the precipitated complex may be washed by adding a washing solution to the precipitate. Wash conditions may be selected to minimize loss of target from the binding element or denaturation of the target during wash or elution. The selection of a washing solution is desired to maintain the stability of the binding of the target to the binding element. The washing solution may be similar to the solution used to select the binding element for the target. The supernatant may be decanted to remove the unbound or non-specifically bound molecules from the sample or any other impurities. Repeated washing may be performed by adding washing solution, such as a buffer and centrifuged followed by decanting the supernatant and collect the precipitate for further processing to release the target. The re-precipitated substrate coupled binding element may be washed, with water or buffer that releases the target to recover the binding element. The precipitate of binding-element target complex or the precipitate of the binding-element may be washed repeatedly to ensure purity of the binding-element target complex or binding element respectively, in different embodiments.

In one or more embodiments, the method further comprises recovering the substrate coupled binding-element. After the target is collected from the supernatant, the precipitate of substrate coupled binding-element may be collected for further processing to recover substrate coupled binding-element. The precipitate may be re-dissolved to form a third solution, wherein the substrate coupled binding-element is recovered from the solution. By recovering the substrate coupled binding element, the method ensures repeated use of the substrate coupled binding-elements.

In one or more embodiments of the method, the substrate coupled binding element is recovered and recycled. In some embodiments, the substrate coupled binding element may be recycled for 2 to 100,000 times. In some other embodiments, the substrate coupled binding element is recycled for 2 to 100 times.

In one or more embodiments of the method, the polymer bound binding element is recycled for multiple times. The binding element may be recycled for 2 to 100,000 times, in some other embodiments, the binding element may be recycled for 2 to 100 times. The structural integrity of the substrate coupled binding element remains intact, which ensures binding efficiency of the binding element to the target for multiple cycles. The term, "cycles" used herein to describe a complete event that is combination of the binding event and the elution event. The recovery of the target and the substrate coupled binding element separately from the precipitated complex under a mild condition is interchangeably used herein as "elution". In case of multiple cycles, for example, a target binds to the binding element and followed by elution of the target from the binding element leaving the binding element free for next target to bind, the complete process refers to a complete cycle. Depending on efficiency of the binding element, the number of cycles can be repeated. As the binding elements are coupled with a substrate, the substrate may also maintain the structural integrity for multiple uses.

The method may enable detecting plurality of targets using a plurality of binding elements. In some embodiments, the method comprises adding a plurality of substrate coupled binding elements to the sample comprising a plurality of targets to form a plurality of substrate coupled binding element-target complexes, followed by precipitating the substrate coupled binding element-target complexes by changing one or more environmental conditions of the substrate and recovering the targets and the substrate coupled binding-elements separately from the precipitated complex under mild conditions. In some embodiments, the method is a part of the single-use manufacturing operations. The method may be a part of the batch manufacturing operations. The method may be a part of the continuous or semi-continuous manufacturing operations.

In one embodiment, the method of recovering a target from a sample is achieved under sterile biopharmaceutical manufacturing process. In this embodiment, the substrate coupled binding-element and target is recovered separately from the precipitated complex under mild condition for one or more times maintaining sterility of the manufacturing process.

In one or more embodiments, the binding element-target complex is washed with a washing solution. The washing may remove un-bound or non-specifically bound molecules present in the sample, or any impurities present in the solution comprising the binding element-target complex. In one or more embodiments, the washing comprises repeated washing cycles. Repeated washings may ensure presence of only specifically bound target to the binding element. In these embodiments, washing solution is used for washing the complex. The post-wash liquid may be removed to eliminate any un-bound target, non-specifically bound other molecules or any impurities.

In one or more embodiments, a washing event and an elution event are different. A washing event is wash with a buffer that maintains binding of target to the binding element, wherein the wash buffer may be similar buffer that used to select the binding element. Washing is included to remove non-targets that are either physically entrapped or non-specifically bound non-targets. In these embodiments, the elution solutions are used to dissociate the target from the binding element. The solutions generally used for elution may be different from the solutions used to select the binding element for the target. For example, water, weak base, or solution comprising chelators, chaotrope or salt may be used for eluting solutions.

As noted, in one or more embodiments, the method further comprises eluting the target from the complex. In some embodiments, the elution is achieved by one or more of the methods selected from: re-constituting the substrate coupled binding element-target complex in a solution to dissociate the target, washing the complex with either a buffer with a high ionic strength or using mild conditions, inducing a conformational change to the binding element or binding element-target complex. In some embodiments of the method, the target eluted from the binding element-target complex by dissociation. The dissociation may be achieved by inducing a conformational change to the binding element or the binding element-target complex or combinations thereof by using water, using a base-solution, such as 0.1-50 mM NaOH, using salt solution, such as 0.5-2M NaCl, using a metal chelators, a chaotropic salts, or combinations thereof. In some embodiments, the conditions for precipitation of substrate bound binding element target complex and dissociation of target from the substrate bound binding element target complex are mutually independent procedure. In these embodiments, the conditions for precipitation and dissociation are independent of each other.

The elution may cause structural change to the binding element to release the target. The elution method ensures a minimum or no structural or functional change to the target. In some embodiments, a conformational change is induced to the binding element to release the target, wherein the target retains the intact structure and function. In some embodiments, a minimum structural change may result in the target, wherein the change is a reversible conformational change. In these embodiments, the target regains its original structure after recovery and re-constitution. For example, a target, such as a protein has a minimum conformational change during recovery with water or a buffer with low ionic strength. The protein target regains its original structure and function, when the target is reconstituted in a buffer with desired ionic strength.

In one or more embodiments, the binding element is coupled to a substrate, wherein the substrate comprises a polymer, a protein, a peptide, a carbohydrate, a small molecule or combinations thereof. In some embodiments, the substrate comprises a stimuli-responsive polymer. The stimuli-responsive polymer may comprise a thermo-responsive polymer, a pH responsive polymer, a pressure responsive polymer, a humidity responsive polymer, an ionic strength responsive polymer, a light responsive polymer or combinations thereof. In some embodiments, the substrate comprises dual responsive polymer, such as a thermoresponsive polymer, which is also responsive to pH.

In one embodiment, the substrate comprises a thermoresponsive polymer. The non-limiting examples of thermoresponsive polymer may include poly(N-vinyl caprolactam), poly(N-isopropylacrylamide) (pNIPAAM) or combinations thereof. Several thermoresponsive polymers have been investigated; the LCST of 32° C. for pNIPAAM makes it more suitable for use in biological systems. The LCST of 32° C. is in a range compatible with the thermo stability of the majority of biomolecules.

In the embodiment, wherein the substrate comprises a thermoresponsive polymer, the binding element-target complex is precipitated by heating the first solution to a temperature above LCST of the thermo-responsive polymer. The results in a precipitation of the polymer coupled binding-element, as heating above LCST renders the polymer more hydrophobic and thus less soluble in aqueous solution. In some embodiments, the re-precipitation of the substrate coupled binding-element is achieved by heating the second solution to a temperature above LCST of the thermo-responsive polymer.

The target molecule may be an organic molecule, an inorganic molecule, a synthetic molecule or combinations thereof. In one or more embodiments, the target molecule may be a protein, a post-translationally modified protein, a peptide, a carbohydrate, a drug, a carrier, a small molecule, an adapter or combinations thereof. The term "carrier" refers to a compound that may attach to one or more drug, protein, peptide, carbohydrate, lipid, genetic material or small molecule for targeted delivery and controlled release. The carrier may include a synthetic compound or a natural compound isolated from different sources. The carrier may be a nanoparticle. In one embodiment, the target molecule is a protein or peptide. For example, the target molecule is a thrombin. The target molecules may be present in a solution, an extract or a formulation, which may be present in a sample at a concentration, ranged between 1 pM and 1 mM, or between 1 mg to 20 g per liter. In one or more embodiments, the target is used for personalized medicine applications, on-demand vaccine manufacturing applications, small-scale pharmaceutical manufacturing, large-scale pharmaceutical manufacturing, pilot-scale pharmaceutical manufacturing.

In one or more embodiments, the binding-elements function as affinity ligands and are selected for high affinity binding to molecular targets, wherein the oligomers are selected for synthesizing binding-elements. In some embodiments, the binding-element is an oligonucleotide sequence, a DNA sequence, an RNA sequence, a PNA sequence, a peptide sequence or combinations thereof. The binding-element may comprise a protein binding sequence or one or more tandem repeat sequences or one or more protein binding sequences. The binding-elements may be up to 100 nucleotides in length. In some embodiments, the binding-elements are ranging between 15-60 nucleotides in length. The binding element may include substitutions on the base portion of DNA to enhance hydrophobic interactions with target molecules. In an exemplary embodiment, the binding element comprises DNA aptamer, which is attractive for its pH and thermal stability, small size (~13 kDa), and high binding efficiency. DNA aptamers may be considered as an efficient affinity binder in the context of downstream processing. The ease of binding element synthesis may be an additional benefit, since it allows synthesizing a less expensive binding element compared to its protein-based counterparts, in addition to reproducibility in synthesis process. A further favorable characteristic of DNA binding element is easy manipulation that disrupts the secondary structure of the binding element which leads to dissociation of the target from the binding element, enabling recovery of the target molecule using mild elution conditions.

The method of affinity precipitation using binding-elements in the presence of target molecules is schematically illustrated in FIG. 1. In an exemplary embodiment, the process flow of affinity precipitation 10 is achieved using the thermoresponsive polymer 14 coupled aptamer 12. The thermoresponsive polymer 14 covalently bound to the aptamer 12 to form a thermoresponsive polymer coupled aptamer 16. In this embodiment, the thermoresponsive polymer coupled aptamer 16 is added to a sample comprising specific target molecules 18 and non-specific molecules 20, as shown in step I. In step II, the thermoresponsive polymer coupled aptamer 16 having affinity to target molecules, efficiently bind the specific target 16 in solution to form a thermoresponsive polymer coupled aptamer-target complex 22, at a temperature below LCST of the thermoresponsive polymer 14. In step III, the solution is heated to reach a temperature above LCST, which renders the thermoresponsive polymer 14 more hydrophobic and thus less soluble in aqueous solution. This results in forming thermoresponsive polymer coupled aptamer-target complex precipitate 24, wherein the non-specific molecules 20 remain in the supernatant. In step IV, the supernatant comprising non-specific molecules 20 may be separated by centrifugation or filtration. In some embodiments, the precipitate 24 is washed repeatedly to remove any impurities, such as any unbound or non-specifically bound molecules. In step V, the precipitate 24 is re-dissolved below the LCST, and the target is released from the aptamer by various methods, such as by washing with deionized water, weak base, salt solution or use of a chelator. Step VI comprises re-precipitating the thermoresponsive polymer coupled binding element 16 by heating the solution above LCST (comprising binding element 16 and released target 18), which results in forming a supernatant, wherein the target 18 is retained in the supernatant. The purified target 18 is recovered for downstream applications.

Example 1: Covalent Linkage of Binding Elements to Thermo-Responsive Polymer

Figure 2:
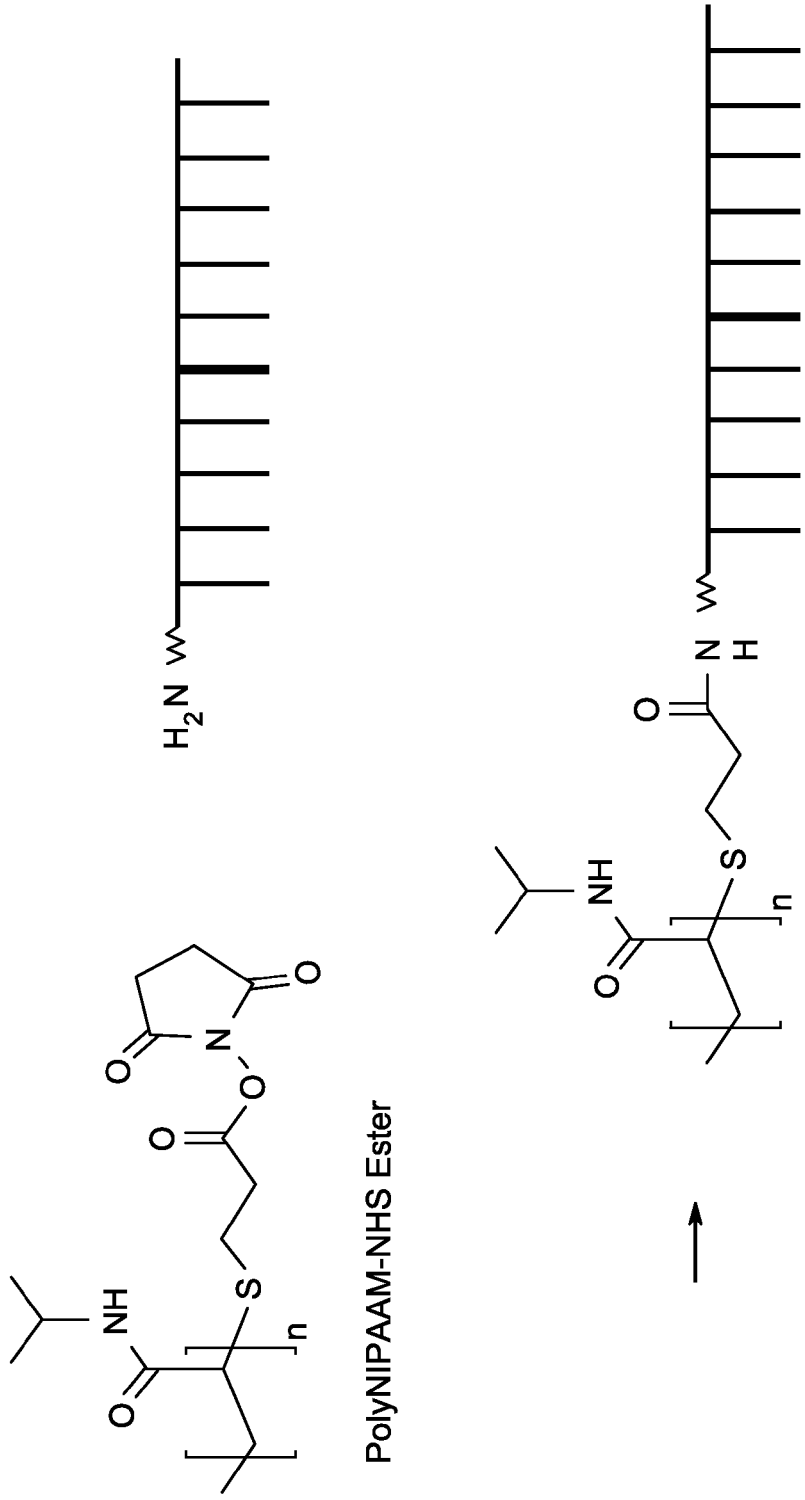
FIG. 2 is a coupling reaction scheme for coupling of oligonucleotides with NHS-pNIPAAM.

N-hydroxysuccinimide (NHS) ester terminated pNIPAAM with number average molecular weight ~2000 g/mole is purchased from Sigma-Aldrich, and that is chemically coupled to an ODN with an amino-end group (FIG. 2) to form the desired conjugate.

The coupling reaction is carried out in an aqueous solution using a slightly basic borate buffer (pH~8.5) at ~4° C.

The coupling reaction is optimized by carefully adjusting the ratio of the pNIPAAM-NHS ester and ODN. The efficiency of the coupling reaction is evaluated with nuclear magnetic resonance (NMR), using signatures of the NHS ester of the free pNIPAAM-NHS ester relative to the peak from the proton on the amide in the conjugate. The efficiency of the coupling reaction can also be quantified using a gel retardation assay. Small aliquots of the coupling reaction solution are examined for differential mobility using gel electrophoresis.

The LCST of the polymer is determined spectroscopically. The optical transmittance of 1.0 w/v % solutions of the polymer in various physiologically relevant aqueous conditions (phosphate buffered saline, at pH=7.4, Citrate-phosphate buffer at pH=5) are monitored at 500 nm with a UV-Vis spectrophotometer as a function of temperature. With a temperature gradient of 0.1° C./min., LCST is determined as the temperature at which transmission drops to 90%.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method of recovering a protein target from a sample, comprising:
adding a thermo-responsive polymer coupled binding element to the sample comprising the protein target to form a liquid thermo-responsive polymer coupled binding element-target complex in solution state;
precipitating the liquid thermo-responsive polymer coupled binding element-target complex out of solution state by changing a temperature of a solution containing the liquid thermo-responsive polymer coupled binding element above a lower critical solution temperature (LCST) of the thermo-responsive polymer to form a precipitated complex; and
recovering the protein target and the thermo-responsive polymer coupled binding element separately from the precipitated complex under a mild elution condition to obtain a recovered target and a recovered thermo-responsive polymer coupled binding element,
wherein a binding element of the thermo-responsive polymer coupled binding element and the recovered thermo-responsive polymer coupled binding element is an aptamer,
wherein the binding element comprises a protein binding sequence for binding the protein target,
wherein the thermo-responsive polymer of the thermo-responsive polymer coupled binding element has the LCST in a range of 30° C.-35° C.; and
wherein recovering the protein target is achieved by dissociating the thermoresponsive polymer coupled binding element-target complex by inducing a conformational change to the binding element, or the thermoresponsive polymer coupled binding element-target complex, or a combination thereof by using mild conditions selected from water, weak base, salt solution, metal chelators, chaotropic salts, or combinations thereof.

2. The method of claim 1, wherein the recovered thermo-responsive polymer coupled binding element is used for repeated cycles of 2 to 100.

3. The method of claim 1, wherein the recovered thermo-responsive polymer coupled binding element is used for repeated cycles of 2 to 1,000,000.

4. The method of claim 1, wherein the thermo-responsive polymer coupled binding element is re-precipitated by heating to a temperature above the LCST of the thermo-responsive polymer.

5. The method of claim 1, wherein the thermo-responsive polymer coupled binding element comprises two or more thermo-responsive polymers.

6. The method of claim 1, wherein the target comprises cells, cellular organelle, organic molecules, inorganic molecules, synthetic molecules or combinations thereof.

7. The method of claim 1, wherein the recovered target is used for personalized medicine applications, on-demand vaccine manufacturing applications, small-scale pharmaceutical manufacturing, large-scale pharmaceutical manufacturing, or pilot-scale pharmaceutical manufacturing.

8. The method of claim 1, wherein the thermoresponsive polymer coupled binding element binds to the protein target by covalent interactions, ionic interactions, H-bonding, Van der Waal's forces, or combinations thereof.

9. The method of claim 1, wherein the method is a part of a single-use manufacturing operations.

10. The method of claim 1, wherein the method is a part of the batch manufacturing operations.

11. The method of claim 1, wherein the method is a part of the continuous or semi-continuous manufacturing operations.

12. The method of claim 1, further comprising washing the precipitated complex to remove unbound molecules or non-specifically bound molecules of the sample to form a washed precipitated complex.

13. The method of claim 12, further comprising re-suspending the washed precipitated complex in a solution.

14. The method of claim 1, further comprising re-precipitating the thermo-responsive polymer coupled binding element after mild elution by changing temperature to form a supernatant comprising the target.

15. The method of claim 14, wherein the protein target is recovered from the supernatant by freeze drying, evaporation, centrifugation, filtration, chromatography, or combinations thereof.

16. The method of claim 1, wherein a binding element of the thermoresponsive polymer coupled binding element is a DNA sequence.

17. The method of claim 16, wherein the binding-element comprises one or more modified bases.

18. A method of recovering a protein target from a sample, comprising:
providing a thermo-responsive polymer-coupled binding element in contact with the sample comprising the protein target to form a liquid thermo-responsive polymer coupled binding element-protein target complex in solution state;
precipitating the liquid thermo-responsive polymer-coupled binding element-protein complex out of solution state to form a precipitated complex;
washing the precipitated complex to remove unbound or non-specifically bound molecules;
re-suspending the precipitated complex in a solution and dissociating the complex under a mild condition selected from water, weak base, salt solution, metal chelator, chaotropic salt, or combinations thereof to release the thermo-responsive polymer coupled binding element and the protein target;

re-precipitating the thermo-responsive polymer-coupled binding element to form a supernatant comprising the protein target; and recovering the protein target from the supernatant to form a recovered target, wherein a binding element of the thermo-responsive polymer coupled-binding element is an aptamer, and wherein the thermo-responsive polymer is poly(N-vinyl caprolactam), poly(N isopropylacrylamide) (pNIPAAM), modified poly(N-vinyl caprolactam), modified pNIPAAM or combinations thereof.

19. The method of claim 18, wherein the protein is recovered from the supernatant by freeze drying, evaporation, centrifugation, filtration, chromatography, or combinations thereof.

20. A method of recovering a plurality of targets from a sample, comprising:
adding a plurality of substrate-coupled binding elements to the sample comprising a plurality of targets to form a plurality of liquid substrate coupled binding element-target complexes in solution state;
precipitating the liquid substrate-coupled binding element-target complexes out of solution state by changing one or more environmental conditions of a substrate of the substrate-coupled binding elements; and
recovering the plurality of targets and the substrate-coupled binding elements separately from the precipitated complex under mild elution conditions by washing the complex with deionized water, dilute base solution, salt solution, a buffer, a chelator, or combinations thereof to obtain a recovered target and a recovered substrate-coupled binding element,
wherein the binding elements of the plurality of substrate-coupled binding elements and substrate-coupled binding elements-target complexes comprise an aptamer, and wherein the binding elements comprise one or more modified bases,
wherein a substrate of the substrate-coupled binding elements comprises a thermo-responsive polymer having a lower critical solution temperature (LCST) in a range of 30° C.-35° C.; and
wherein a target of the plurality of targets comprises a protein, a peptide, a carbohydrate, a small molecule, a carrier, a drug, an epitope or combinations thereof.

21. The method of claim 20, wherein the substrate comprises two or more thermo-responsive polymers with different lower critical solution temperatures (LCSTs).

22. The method of claim 20, wherein the target comprises cells, cellular organelle, organic molecules, inorganic molecules, synthetic molecules or combinations thereof.

23. The method of claim 20, wherein the recovered target is used for personalized medicine applications, on-demand vaccine manufacturing applications, small-scale pharmaceutical manufacturing, large-scale pharmaceutical manufacturing, or pilot-scale pharmaceutical manufacturing.

24. The method of claim 20, wherein the binding elements bind to the plurality of targets by covalent interactions, ionic interactions, H-bonding, Van der Waal's forces or combinations thereof.

25. The method of claim 20, wherein the binding element is an RNA sequence.

26. A method of recovering a plurality of targets from a sample, comprising:
adding a plurality of substrate-coupled binding elements to the sample comprising a plurality of targets to form a plurality of liquid substrate coupled binding element-target complexes in solution state;
precipitating the liquid substrate-coupled binding element-target complexes out of solution state by changing one or more environmental conditions of a substrate of the substrate coupled binding elements; and
recovering the plurality of targets and the substrate-coupled binding elements separately from the precipitated complex under mild elution conditions by washing the complex with deionized water, dilute base solution, salt solution, a buffer, a chelator, or combinations thereof to obtain a recovered target and a recovered substrate-coupled binding element,
wherein the binding elements of the plurality of substrate-coupled binding elements and substrate-coupled binding elements-target complexes comprise an aptamer, and wherein the binding elements comprise one or more modified bases,
wherein a substrate of the substrate-coupled binding elements comprises a thermo-responsive polymer having a lower critical solution temperature (LCST) in a range of 30° C.-35° C., and
wherein a target of the plurality of targets comprises a protein, a peptide, a carbohydrate, a small molecule, a carrier, a drug, an epitope or combinations thereof.

* * * * *